United States Patent

Peshkovskiy et al.

(10) Patent No.: US 7,156,201 B2
(45) Date of Patent: Jan. 2, 2007

(54) ULTRASONIC ROD WAVEGUIDE-RADIATOR

(75) Inventors: Sergey L. Peshkovskiy, New York, NY (US); Michael L. Friedman, Wayne, NJ (US); Wilton A. Hawkins, Montclair, NJ (US)

(73) Assignee: Advanced Ultrasonic Solutions, Inc., Lords Valley, PA (US)

(*) Notice: Subject to any disclaimer, the term of this patent is extended or adjusted under 35 U.S.C. 154(b) by 273 days.

(21) Appl. No.: 10/982,588

(22) Filed: Nov. 4, 2004

(65) Prior Publication Data

US 2006/0090956 A1    May 4, 2006

(51) Int. Cl.
- G10K 11/08 (2006.01)
- H03H 9/24 (2006.01)
- H04B 11/00 (2006.01)
- H03H 9/25 (2006.01)

(52) U.S. Cl. .................. 181/175; 381/338; 310/323.19; 333/145

(58) Field of Classification Search .......... 181/175, 181/177, 192, 142; 381/337–340; 310/323.19; 333/145

See application file for complete search history.

(56) References Cited

U.S. PATENT DOCUMENTS

| | | | | |
|---|---|---|---|---|
| 3,184,842 A | * | 5/1965 | Maropis | 228/111 |
| 3,277,404 A | * | 10/1966 | Fabian | 333/145 |
| 3,524,085 A | * | 8/1970 | Shoh | 310/325 |
| 3,546,498 A | * | 12/1970 | McMaster et al. | 310/323.19 |
| 3,568,104 A | * | 3/1971 | Bailey | 333/145 |
| 3,736,532 A | * | 5/1973 | Armenakas | 333/145 |
| 3,891,869 A | * | 6/1975 | Scarpa | 310/325 |
| 3,915,018 A | * | 10/1975 | Karplus | 73/647 |
| 4,131,505 A | * | 12/1978 | Davis, Jr. | 156/580.1 |
| 4,337,843 A | | 7/1982 | Wendel | |
| 4,691,724 A | * | 9/1987 | Garcia et al. | 134/169 R |
| 4,710,668 A | * | 12/1987 | Fima et al. | 310/323.21 |
| 4,896,535 A | * | 1/1990 | Duckart et al. | 73/290 V |
| 5,112,300 A | * | 5/1992 | Ureche | 604/22 |
| 5,241,287 A | | 8/1993 | Jen | |
| 5,269,297 A | * | 12/1993 | Weng et al. | 606/128 |
| 5,289,436 A | | 2/1994 | Terhune | |
| 5,380,274 A | * | 1/1995 | Nita | 604/22 |
| 5,386,169 A | * | 1/1995 | Dubruque | 310/323.19 |
| 5,527,273 A | * | 6/1996 | Manna et al. | 604/22 |
| 5,713,916 A | | 2/1998 | Dias | |
| 5,828,274 A | | 10/1998 | Jen et al. | |
| 6,078,125 A | * | 6/2000 | Roberts | 310/325 |

(Continued)

FOREIGN PATENT DOCUMENTS

GB    2167270 A  *  5/1986

*Primary Examiner*—Edgardo San Martin
(74) *Attorney, Agent, or Firm*—Robert J. Sinnema; Bond, Schoeneck & King, PLLC

(57) ABSTRACT

The present invention comprises an ultrasonic resonant rod waveguide-radiator with at least three cylindrical sections, one of which is an entrance section having a planar entrance surface and another of which is an exit section having a planar exit surface, and at least two sections having a variable cross-section. The cylindrical sections and sections of variable cross-section are arranged in alternating fashion and connected to each other acoustically rigidly. The dimensions of the cylindrical sections and the sections of variable cross-section are selected so that the gain of the waveguide-radiator is significantly greater than unity and the strain created by passage of ultrasonic waves through the waveguide-radiator is minimized, increasing the operational life of the waveguide-radiator and maximizing the amount of useful energy transmitted by the waveguide-radiator.

8 Claims, 7 Drawing Sheets

U.S. PATENT DOCUMENTS 6,400,648 B1    6/2002   Heijnsdijk et al.
6,837,445 B1 *  1/2005   Tsai ........................ 239/102.2
6,841,921 B1 *  1/2005   Stegelmann ........... 310/323.19
7,002,283 B1 *  2/2006   Li et al. ..................... 310/325
2004/0127926 A1  7/2004  Beaupre

* cited by examiner

DO = 50.00 mm; d = 16.67 mm; D1 = 50 mm; L1 = 43.46 mm; L2 = 40.11 mm; L4 = 40.11 mm; L5 = 105.55 mm; K = 6.84; F = 20.0 kHz;

DO = 50.00 mm; d = 16.67 mm; D1 = 41.67 mm; L1 = 40.11 mm; L2 = 20.05 mm; L3 = 28.07 mm; L4 = 4.01 mm; L5 = 3.93 mm; K = 6.14; F = 20.0 kHz;

ULTRASONIC ROD WAVEGUIDE-RADIATOR

BACKGROUND OF THE INVENTION

1. Field of the Invention

The present invention relates to the field of ultrasonic equipment and can be used in different technological devices for the transmission of acoustic energy into an acoustic load, for example, in heat and mass transfer processes, plastic welding, metal treatment, etc.

2. Description of Prior Art

Acoustic energy is usually transmitted into an acoustic load (liquid, polymeric or hard material) using an ultrasonic waveguide-radiator connected to an electro-acoustic transducer (magnetostrictive or piezoelectric). The tasks of the waveguide-radiator are to increase the amplitude of the transducer vibrations A up to the level necessary in a given technology, to match the energy of a transducer to an acoustic load, to uniformly distribute radiated acoustic energy throughout the volume of the medium being treated, and/or to facilitate reliable fastening of cutting and other tools to the waveguide radiator. Matching the energy of the transducer to the acoustic load means the development of a waveguide-radiator design that provides transmission of maximum acoustic power from the transducer into the load.

It is known that specific acoustic power radiated by a waveguide into an acoustic load, for instance into a liquid, is equal to $w=0.5 \rho C \omega^2 A^2$ [Wt/sq.m]. Here $\rho$ is the density of liquid, C is the speed of sound in liquid, $\omega$ is the frequency of ultrasonic vibrations, and A is the amplitude of ultrasonic vibrations. The total acoustic power radiated into liquid is equal to $W=wS$ [Wt]. Here S is the area of the radiating surface of the waveguide-radiator. Thus, it is evident that an increase in the total radiated acoustic power at constant load and frequency can be achieved by increasing either of the following two factors: the amplitude of output vibrations of the waveguide-radiator or the area of the waveguide-radiator's radiating surface. The amplitude of output vibrations cannot be increased above a certain level that corresponds to the fatigue strength of the waveguide-radiator material. Increasing amplitude above this level causes the waveguide-radiator to break down. Furthermore, a considerable increase in the amplitude of vibrations is not always justified from the technological point of view. It is also possible to increase the exit diameter of a rod waveguide-radiator up to a certain level that is equal to about $\lambda/4$ (where $\lambda$ is the wavelength of ultrasound waves in the material of a thin-rod waveguide-radiator). When the waveguide-radiator exit diameter is larger than this value, radiation via the waveguide-radiator's side surfaces begins to have a strong effect, and calculation of the waveguide's acoustic properties becomes difficult to predict. Nevertheless, increasing the waveguide-radiator exit diameter up to a value close to $\lambda/4$ gives an opportunity to increase the radiated power by several times.

The closest device in its essence to the present invention is a known ultrasonic rod waveguide-radiator that has a shape converging (tapering) to a load. The shape of such a waveguide-radiator is determined by the fact that its gain factor of the amplitude of ultrasonic vibrations in the direction of an acoustic load must be higher than unity. To increase the radiating surface, a converging waveguide radiator is provided at the radiating exit end with a section in the form of a thin disk or plate having a large diameter, usually close to the waveguide-radiator entrance diameter. The presence of a short transition section of arbitrary shape between the waveguide radiator and the plate at its radiating end is also possible. This section is designed to increase the area of the exit radiating surface and consequently the acoustic energy radiated into a load.

Such a waveguide-radiator with a plate or disk at the end has substantial disadvantages. First, at a small value of the ratio of the length and diameter of the specified section (usually less than 0.5), instead of the axial (longitudinal) mode of vibrations which must occur in the body of the waveguide-radiator, vibrations of more complex modes (for instance, offaxial mode) arise in it (for example, flexural vibrations). This leads to a disruption of the regime of the operation of the entire waveguide-radiator. Its natural resonance frequency changes and, as a consequence, additional experimental fitting of geometrical dimensions is required. Thus, a direct acoustic calculation of the waveguide-radiator as a waveguide of longitudinal waves becomes inaccurate. This manifests itself particularly clearly at high vibration amplitudes of the specified section of the waveguide-radiator. Second, the length of the specified exit section is small as compared with its diameter and, therefore, in this section the degree of strain (and, as a consequence, stress) along the section length is high, which substantially decreases the operational life span of such a waveguide-radiator at high amplitude.

3. Objects and Advantages

It is therefore a principal object and advantage of the present invention to provide a waveguide-radiator that is free from the drawbacks enumerated above, having an exit diameter close to the entrance diameter, and a gain factor much higher than unity, and having the following objectives:

1. To improve the quality of operation and to increase the operational life of a wave guide-radiator.

2. To increase the acoustic energy radiated into a load by a waveguide-radiator.

3. To increase the reliability of fastening various cutting and other tools on the waveguide radiator.

4. To increase the available radiation surface and the uniformity of the distribution of acoustic energy throughout the volume of an ultrasonic reactor.

5. To conduct ultrasonic treatment of the internal surfaces of thin extended channels and tubes.

6. To increase the intensity of acoustic radiation in the working medium of an ultrasonic reactor.

7. To increase the efficiency of conversion of electric energy of an ultrasonic generator into acoustic energy radiated into a load.

SUMMARY OF THE INVENTION

In accordance with the foregoing objects and advantages, the present invention provides an ultrasonic resonant rod waveguide-radiator with at least three cylindrical sections, one of which is an entrance section having a planar entrance surface and another of which is an exit section having a planar exit surface, and at least two sections having a variable cross-section. The cylindrical sections and sections of variable cross-section are arranged in alternating fashion and connected to each other acoustically rigidly. As described herein, the dimensions of the sections are selected so that the exit surface and entrance surface are approximately equal, the length of the sections of variable cross-section is determined according to a specified formula, and the sum of the length of the exit section and the adjacent section is 30% or more of the total length of the waveguide radiator.

BRIEF DESCRIPTION OF THE DRAWINGS

The present invention will be more fully understood and appreciated by reading the following Detailed Description in conjunction with the accompanying drawings, in which.

DETAILED DESCRIPTION

Figure 1:
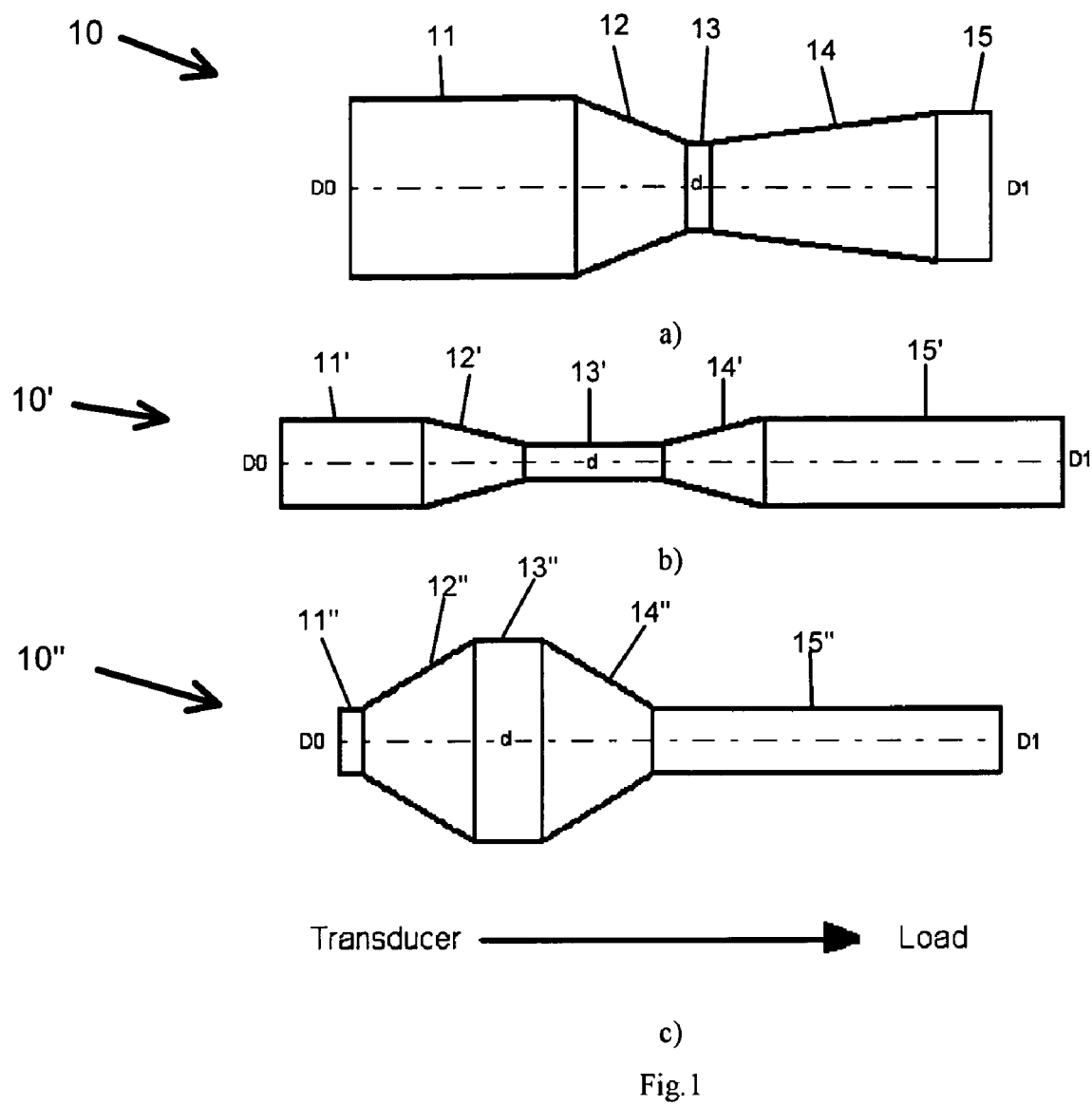
FIG. 1 depicts side elevation views of a waveguide-radiator according to three embodiments of the present invention.

Referring now to the drawings, wherein like reference numerals refer to like parts throughout, there is seen in FIG. 1 a waveguide-radiator 10, 10', 10" according to the present invention. The improvement of the quality of operation and an increase in the operational life of a waveguide-radiator are achieved through the use of a waveguide-radiator shown in FIG. 1. The waveguide-radiator consists of five sections 11–15, 11'–15', 11"–15" in a combination of cylindrical sections 11, 13, 15, 11', 13', 15', 11", 13", 15" and sections of variable cross-section 12, 14, 12', 14', 12", 14", all made of metal. The cylindrical sections and variable cross-section sections alternate in series and are acoustically rigidly connected between themselves. The geometrical dimensions of these sections are selected using a known method of acoustic calculation (Rayleigh equation) in such a way that their total length is equal to the value that is a multiple of half the length of an acoustic wave in the waveguide-radiator material, taking into account a geometrical sound dispersion. That is, the waveguide-radiator must be resonant and also provide a gain factor of the amplitude of vibrations in the direction of an acoustic load significantly higher than unity. The waveguide-radiator sections of variable cross-section have a particular shape: conical, exponential or catenoidal. The lengths of the sections of variable cross-section are approximately equal between themselves and are equal to or more than the following value: $(\text{Log} N)/k$. Here $k=\omega/C$ is the wave number, N is the ratio of the diameters of thick and thin cylindrical sections that are adjacent to the section of variable cross-section. It is known that the specified length of a section of variable cross-section is critical from the standpoint of the passage of a longitudinal acoustic wave. Such selection of the length and shape of a section of variable cross-section allows one to decrease considerably the degree of dynamical strain along the section length and thus to increase the operational life of the waveguide-radiator. Furthermore, because the relation of the length to the diameter of the section is very large, the deformations in perpendicular direction (non-axial modes) are miniscule and the strain is practically an axial one, causing the longitudinal mode of an acoustic wave to be maintained along the entire length of the waveguide radiator. At its exit section, complex modes of vibrations (for instance, bending ones), as in the case of a waveguide according to the prior art, do not arise. In this case, even at very high output amplitudes close to maximum allowable values for the radiator material, the operational life of a waveguide-radiator according to the present invention is several years.

An increase in the total acoustic power radiated into a load is achieved through a special acoustic calculation based on the Rayleigh equation and the design of such a waveguide-radiator whose exit section has a relatively large area of cross-section at the gain factor of the waveguide-radiator much higher than unity. The gain factor of the waveguide-radiator can be much higher than unity, in spite of the diameter $D_1$ of its exit section 15, 15', 15" is close to the diameter $D_0$ of its entrance section 11, 11', 11". (See FIGS. 1A, 1B, 1C.)

Incorporating an exit cylindrical section 15, 15', 15" (FIGS. 1A, 1B, 1C) having a large diameter facilitates easy connection to the waveguide-radiator of different devices that provide a generally uniform acoustic treatment of large volumes and surfaces. A large diameter exit section of the waveguide-radiator, when combined with large amplitude vibrations also facilitates easy connection to the waveguide-radiator of different cutting and other tools used in ultrasonic surgery and treatment of hard materials.

Figure 2:
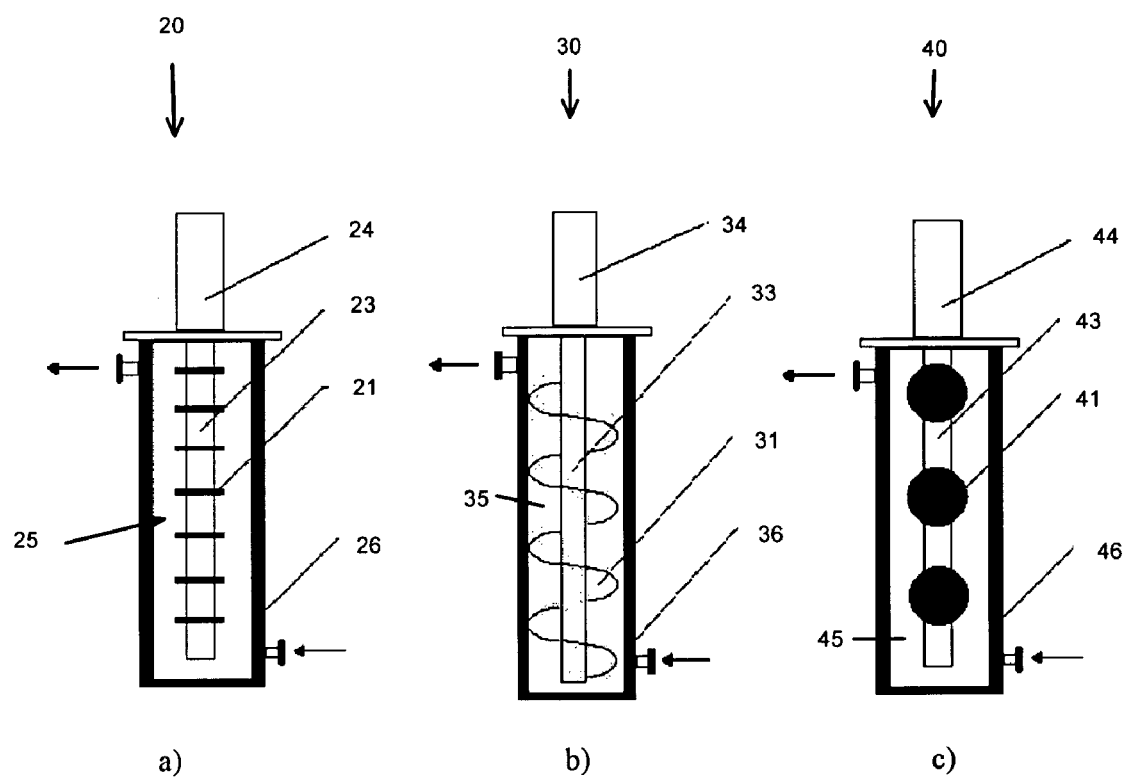
FIG. 2 depicts sectional side elevation views of a waveguide-radiator according to three other embodiment of the present invention.

FIG. 2A shows an ultrasonic device 20, inside of which the specified waveguide-radiator is placed. Resonant thin plates 21 fastened acoustically rigidly to the waveguide-radiator body are positioned at a certain distance from one another on the extended exit section 23 of the waveguide-radiator. The waveguide-radiator is connected to an acoustic transducer 24 and increases the vibration amplitude of the latter. Longitudinal vibrations of the extended exit section 23 of the waveguide-radiator are converted into the flexural vibrations of resonant plates interacting with a liquid acoustic load 25 situated in a reactor 26. In this way, the present invention achieves uniform treatment of a large volume of liquid with high-intensity ultrasound.

FIG. 2B shows an ultrasonic device 30, inside of which the specified waveguide-radiator with an extended exit section 33 is also placed. The extended exit section 33 of the waveguide-radiator is provided with a thin plate 31 fixed on its side surface in a helical fashion in such a way that the radiating surfaces of the plate 31 are positioned at an acute angle to the axis of the rod waveguide 33. The waveguide-radiator is connected to an acoustic transducer 34 and increases the vibration amplitude of the latter. Longitudinal vibrations of the extended exit section 33 of the waveguide-radiator are converted into the flexural vibrations of the specified thin plate 31 interacting with a liquid acoustic load 35 situated in a reactor 36. In this way, the present invention achieves uniform treatment of a large volume of liquid with high-intensity ultrasound.

FIG. 2C shows an ultrasonic device 40, inside of which the specified waveguide-radiator with an extended exit section 43 is also placed. The extended exit section of the waveguide-radiator is provided with several resonant spheres 41 that are acoustically rigidly connected to the waveguide radiator. The waveguide-radiator is connected to an acoustic transducer 44 and increases the vibration amplitude of the latter. Longitudinal vibrations of the extended exit section of the waveguide-radiator are converted into the radial vibrations of the specified spheres interacting with a liquid acoustic load 45 situated in a reactor 46. In this way, the present invention achieves uniform treatment of a large volume of liquid with high-intensity ultrasound.

It should be noted that the total area of radiating plates, helical side plate and radiating spheres is very large and thus overcomes the theoretical limitations of previous waveguide designs, and therefore produces a maximum increase in the total acoustic power radiated into a liquid.

Figure 3:
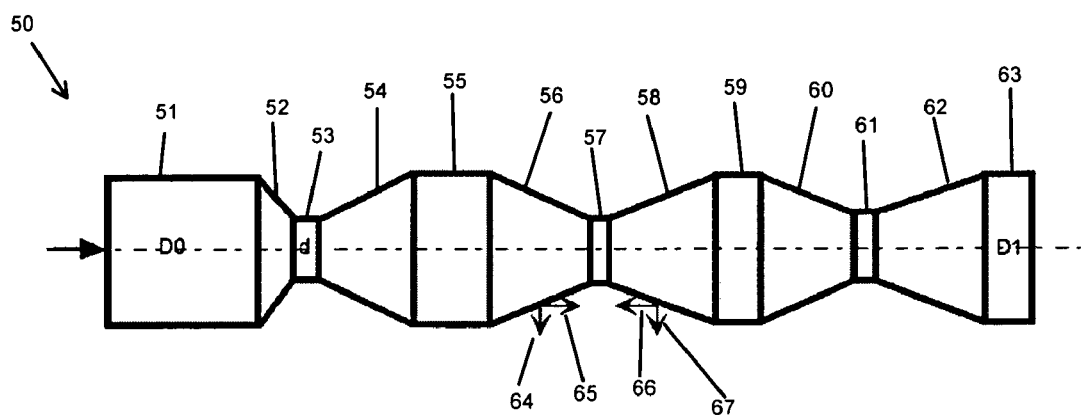
FIG. 3 is a side elevation view of a waveguide-radiator according to another embodiment of the present invention.

As set forth above, conventional ultrasonic rod waveguide-radiators have a theoretical limitation on their diameter, which does not allow the radiated energy to be considerably increased by increasing the device's diameter. To overcome this limitation, a modification of the disclosed waveguide-radiator shown in FIG. 3 was developed. In the given modification of the disclosed waveguide-radiator 50, radiation occurs from its side surface that is made in the form of alternating cylindrical sections (51, 53, 55, 57, 59, 61, 63) and sections of variable cross-section (52, 54, 56, 58, 60, 62). The surfaces of the sections of variable cross-section have components 64, 67 of the amplitude of vibrations that are directed perpendicular to the waveguide-radiator axis. In addition, the lengths of the waveguide radiator sections are calculated in such a way that the components 65, 66 of the vibration amplitude of the sections of variable cross-section that are directed along the waveguide axis are oriented toward each other. In this manner, a strong lateral radiation of the waveguide-radiator is achieved. Since there are no theoretical limitations on the waveguide-radiator length, the total area of its side radiating surface can be large. The total acoustic energy radiated into a liquid can be also substantially increased over the prior art.

Figure 4:
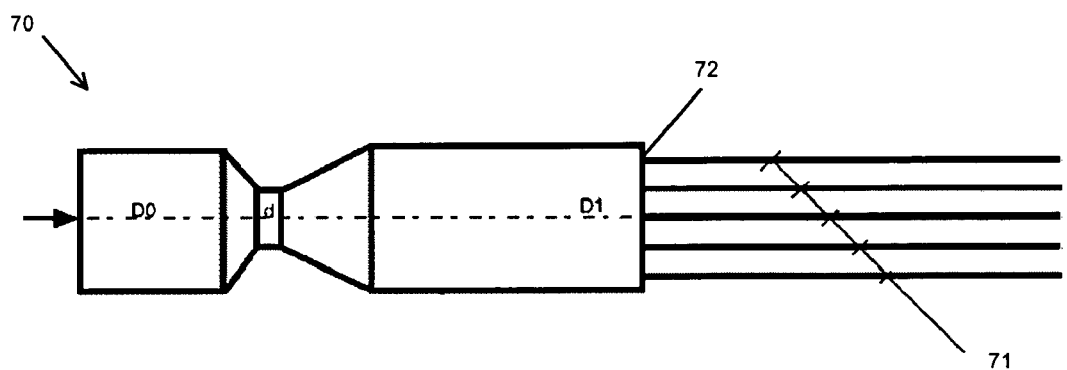
FIG. 4 is side elevation view of a waveguide-radiator according to another embodiment of the present invention.

In ultrasonic practice there are cases when ultrasonic treatment must be conducted inside narrow long tubes, channels or slots. For such cases, the following modification of the specified waveguide-radiator 70 can be used. See FIG. 4. One or several long flexible rods 71 whose ratio of length to diameter is significantly greater than 100 are connected acoustically rigidly to the transverse exit surface 72 of the waveguide-radiator 70. During the operation of the ultrasonic waveguide radiator, longitudinal ultrasonic vibrations of large amplitude are transmitted to the specified flexible rods also in the longitudinal direction. It is known that at a certain critical amplitude of longitudinal vibrations a long rod loses its mechanical stability and begins to vibrate in a bending mode. Therefore its side surface also becomes a source of ultrasonic radiation into a liquid, and this radiation can be used for technological purposes inside narrow extended channels, into which the rod is introduced, for example, for the cleaning of their walls.

Figure 5:
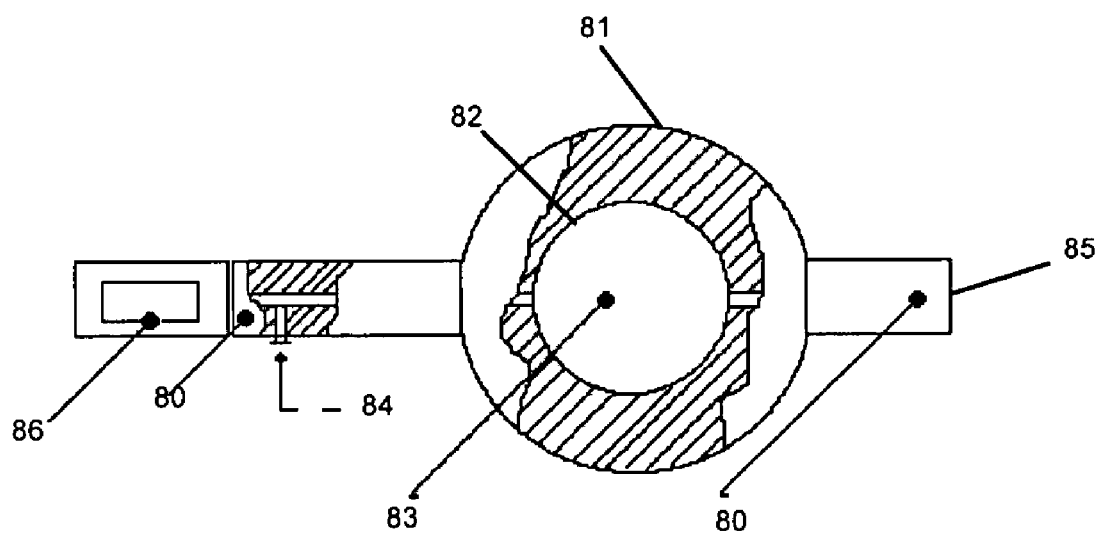
FIG. 5 is a partial sectional side elevation view of a waveguide-radiator according to another embodiment of the present invention.

It was stated above that because of limitations on the fatigue strength of a metal, there is an upper limit to the amplitude of the vibrations of a waveguide-radiator, at which the waveguide-radiator rapidly breaks down mechanically and its operational life sharply decreases. This phenomenon also limits the possibility of increasing the acoustic power radiated into a load using a conventional waveguide. To overcome this basic obstacle and to increase further the acoustic energy radiated into a load, the following modification of a waveguide-radiator according to the present invention was developed. As shown in FIG. 5, a waveguide radiator 80 according to the present invention has an ultrasonic reactor 81 arranged immediately inside the waveguide-radiator 80 in the form of a hollow resonant sphere 82 acoustically rigidly connected to it and being an integral part of it. The resonant sphere 82 is filled with a working liquid or gas (acoustic load) 83. The waveguide radiator also includes an inlet 84 and outlet 85 for the acoustic load 83, and is connected to a transducer 86. The acoustic parameters of the resonant sphere 82 are selected such that the focus of the acoustic field inside the sphere is located in its geometric center. Thus, in the geometric center of the sphere a very high amplitude of vibrations in a load can be achieved due to concentration of the vibrations in a converging acoustic wave.

Figure 6:
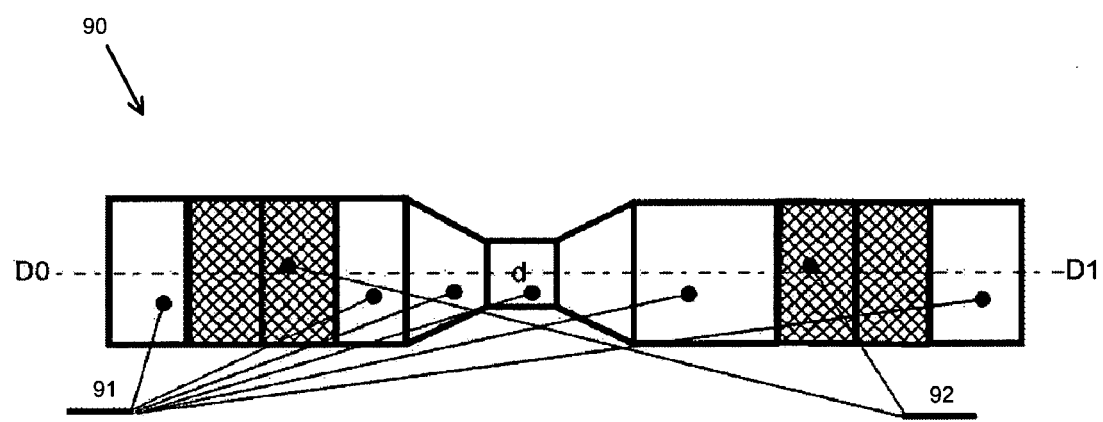
FIG. 6 is side elevation view of a waveguide-radiator according to another embodiment of the present invention.

Another embodiment of a waveguide-radiator 90 according to the present invention is shown in FIG. 6. According to other embodiments of the present invention, the waveguide-radiator is passive. That is, it does not have inside itself an active acoustic transducer for converting electric energy into acoustic energy. According to the present embodiment of the invention, the waveguide-radiator 90 also performs an active function, the conversion of electric energy into acoustic energy. Acoustic calculation of the geometrical parameters of the waveguide radiator in the given case is carried out taking into account not only the passive properties of the cylindrical sections and sections of variable cross-section all comprised of standard waveguide-radiator material 91, but also the active properties of piezoelectric annular transducers 92 connected acoustically rigidly to the waveguide-radiator. Piezoelectric annular transducers 92 are situated in the waveguide-radiator cross-sections close to nodal cross-sections. Because the number of nodal cross-sections of the specified waveguide-radiator can be greater than one, the number of the pairs of piezoelectric rings 92 can also be increased manifold in comparison with known piezoelectric transducers. Thus, the total power of the waveguide-radiator also increases manifold. In addition, because an active waveguide-radiator according to this embodiment has a gain factor greater than unity, the amplitude of the vibrations at its exit end is much higher than the amplitude of the vibrations of the piezoelectric annular transducers themselves.

For calculation of a waveguide-radiator according to the present invention, the following initial parameters are taken. The waveguide-radiator material is titanium (Ti-6AL-4V), the operating frequency F=20 kHz, the gain factor of the amplitude of vibrations K≈6, and the entrance and exit diameters of the waveguide-radiator are approximately equal. The ratio of the total length of the waveguide radiator sections L4+L5 to its exit diameter is about 3:1.

Figure 7:
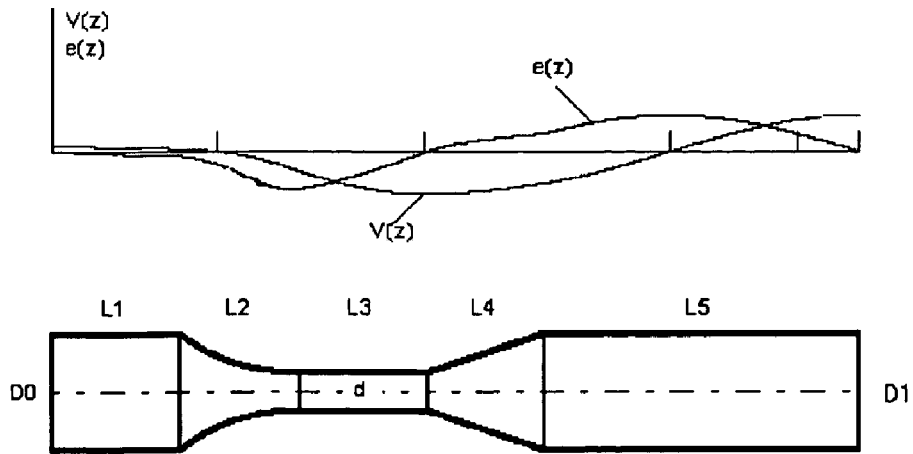
FIG. 7 is a graph depicting the amplitude and strain of a wave passing through a waveguide-radiator according to the present invention.

FIG. 7 shows the following calculated parameters for a resonant waveguide-radiator: diameters D0, d, D1; lengths of cylindrical sections L1, L3, L5; lengths of the sections of variable cross section L2, L4. Besides, FIG. 7 shows the plots of the distribution of the vibration amplitudes V(z) and strain e(z) along the waveguide-radiator length, which were also obtained as a result of calculation.

Figure 8:
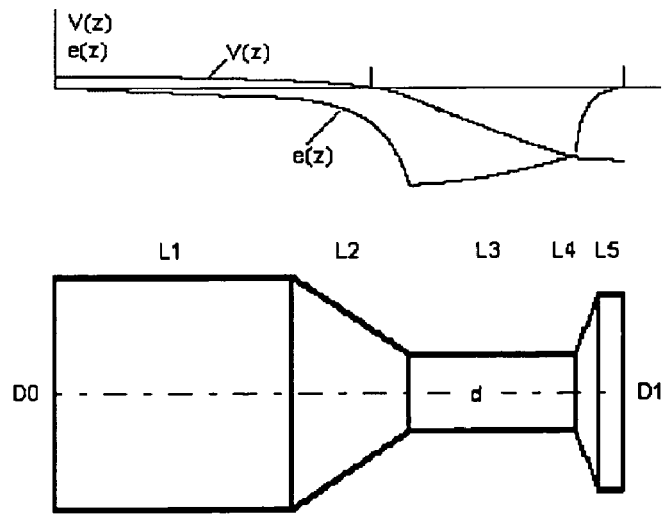
FIG. 8 is a graph plotting the amplitude and strain of a wave passing through a waveguide-radiator according to the prior art.

In order to allow the comparison of the results of calculation of the specified waveguide-radiator with analogous calculated data for a conventional waveguide (so called spool horn), FIG. 8 is given. The ratio of the total length of the conventional waveguide sections L4+L5 to its exit diameter is about 0.2:1.

From comparison of FIG. 7 and FIG. 8 it is seen that the course of the distribution of strain e(z) along the length of the conventional waveguide shown in FIG. 8 has a discontinuous, polygonal character, which is indicative of high values of the strain and stress gradients in the conventional waveguide body. At the same time, the course of analogous curve e(z) for the waveguide-radiator according to the present invention has a smooth character without sharp bends and kinks. This points to the absence of considerable gradients of strain and stresses in the body of the waveguide radiator according to the present invention. The absence of high local gradients of mechanical stresses in the body of the disclosed waveguide-radiator provides a considerable increase in the limit of its fatigue strength and, as a consequence, its expected operational life in comparison with the conventional waveguide at equal parameters and conditions of their operation.

On the basis of the data given in FIG. 7 and FIG. 8, the disclosed waveguide-radiator shown in FIG. 7 and the conventional waveguide shown in FIG. 8 were manufactured and tested. Tests were carried out at equal amplitudes of vibrations at the exit ends of the waveguides and being 150 µm peak-to-peak. The acoustic load was tap water. The results of tests showed the following:

1. The disclosed waveguide-radiator (FIG. 7) had an actual resonance frequency that corresponded closely with the predicted one and an actual gain factor that corresponded closely with the predicted one. It operates stably. Moreover, the disclosed waveguide was tested for 6 (six) month of continuous work without failure; after this time the tests were stopped.

2. The conventional waveguide (FIG. 8) operated unstably. The actual waveguide resonance frequency differed from the predicted one (which was calculated in advance). The exit section L5 had a considerable bending mode of vibrations. It was necessary to conduct an incremental tuning of this waveguide to obtain its resonance length. Only after such tuning was it possible to test the waveguide. The operating time of the conventional waveguide after its additional tuning was about 6 days, at which point it suffered mechanical failure.

The theory of acoustic waveguide-radiators is based on the problem of longitudinal vibrations of multi-section rods that have cylindrical sections and sections of variable cross-section. We will consider only waveguide-radiators of axially symmetric shape. Other types of waveguide-radiators (for example, wedge-shaped) can be considered in the analogous way.

Figure 9:
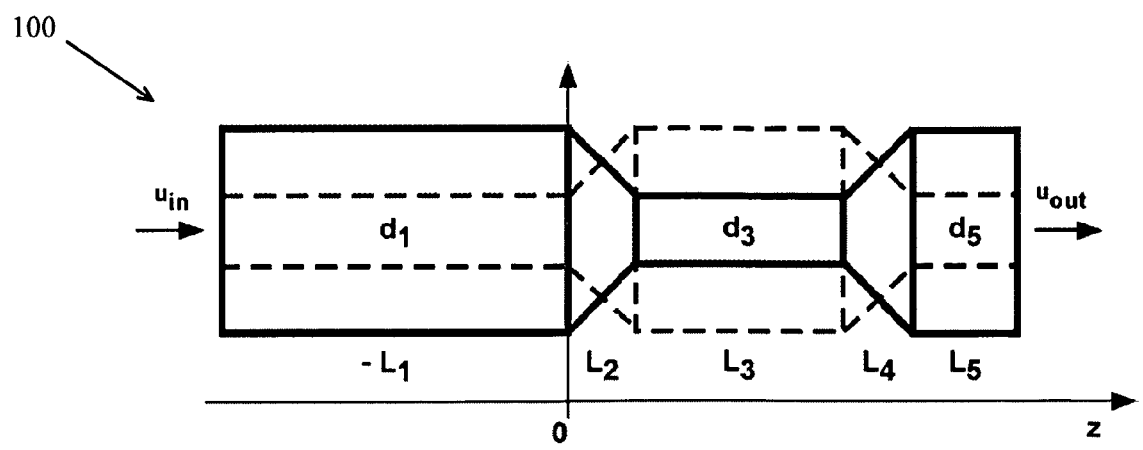
FIG. 9 is a side elevation view of a waveguide-radiator according to an embodiment of the present invention.

We assume that during the passage of the stress waves through a waveguide-radiator, the wave front remains plane, while the stresses are uniformly distributed over the waveguide-radiator's cross-section. This assumption limits us to the consideration of only thin waveguide-radiators, whose resonance length significantly exceeds their diameter. The scheme and the designation of parameters for an exemplary five-section rod waveguide-radiator are given in FIG. 9, which depicts a rod waveguide-radiator 100 having five sections of length $L_N$ and diameter $d_N$, where N is the number of the section. Two possible situations are presented: a waveguide-radiator for which $d_1/d_3>1$ is shown by the solid line; a waveguide-radiator for which $d_1/d_3<1$ is shown by the dotted line. In the approximation used, the problem is considered in one dimension, and it is limited to the consideration of sections with variable cross-section of only conical shape. For steady-state mode, the Rayleigh equation of vibrations for displacements u takes the following:

$$u'' + \frac{1}{S}S'u' + k^2 u = 0. \tag{1}$$

Here: $k=\omega/C$ is the wave number, $\omega=2\pi f$ is the angular frequency of vibrations, and f is the frequency of vibrations.

The solution of equation (1) for the waveguide-radiator sections can be written as:

$u_1 = A_1 \cos kz + B_1 \sin kz -L_1 < z < 0$ $u_2 = F(A_2 \cos kz + B_2 \sin kz)\ 0 < z < L_2$ $u_3 = A_3 \cos kz + B_3 \sin kz\ L_2 < z < L_2+L_3$ $u_4 = F(A_4 \cos kz + B_4 \sin kz)\ L_2+L_3 < z < L_2+L_3+L_4$ $u_5 = A_5 \cos kz + B_5 \sin kz\ L_2+L_3+L_4 < z < L_2+L_3+L_4+L_5$ Then, using the boundary conditions for the waveguide-radiator sections, we obtain the system of equations for displacements u and strains u'.

At $z=-L_1$, $u_1=u_{in}$, $ES_1 u'_1 = -F_{in}$, $F_{in}=0$ $A_1 \cos kL_1 - B_1 \sin kL_1 = u_{in}$;

$EkS_1(A_1 \sin kL_1 + B_1 \cos kL_1) = -F_{in}$.

At $z=0$, $u_2=u_1$, $u'_2=u'_1$.

$FA_2 = A_1$;

$F'A_2 + FB_2 k = kB_1$;

$\alpha = (d_1-d_3)/L_2 d_1$;

$F=2/d_1$; $F'=F\alpha$.

At $z=L_2$, $u_3=u_2$, $u'_3=u'_2$.

$A_3 \cos kL_2 + B_3 \sin kL_2 = F(A_2 \cos kL_2 + B_2 \sin kL_2)$;

$-kA_3 \sin kL_2 + kB_3 \cos kL_2 = (F'B_2-FkA_2)\sin kL_2 + (F'A_2 FkB_2)\cos kL_2$;

$\alpha = (d_1-d_3)/L_2 d_1$;

$F=2/d_3$; $F'=-F/(L_2-1/\alpha)$.

At $z=L_2+L_3$, $u_4=u_3$, $u'_4=u'_3$.

$F[A_4 \cos k(L_2+L_3)+B_4 \sin k(L_2+L_3)] = A_3 \cos k(L_2+L_3)$;

$(F'B_4-FkA_4)\sin k(L_2+L_3)+(F'A_4+FkB_4)\cos k(L_2+L_3) = -kA_3 \sin k(L_2+L_3)+kB_3 \cos k(L_2+L_3)$;

$\alpha = (d_3-d_5)/L_4 d_3$;

$F=2/d_3$; $F'=F\alpha$.

At $z=L_2+L_3+L_4$, $u_5=u_4$, $u'_5=u'_4$.

$A_5 \cos k(L_2+L_3+L_4)+B_5 \sin k(L_2+L_3+L_4) = F[A_4 \cos k(L_2+L_3+L_4)+B_4 \sin k(L_2+L_3+L_4)]$;

$-kA_5 \sin k(L_2+L_3+L_4)+kB_5 \cos k(L_2+L_3+L_4) = (F'B_4-FkA_4)\sin k(L_2+L_3+L_4)+(F'A_4+FkB_4)\cos k(L_2+L_3+L_4)$;

$\alpha = (d_3-d_5)/L_4 d_3$;

$F=2/d_5$; $F'=-F/(L_4-1/\alpha)$.

At $z=L_2+L_3+L_4+L_5$, $u_5=u_{out}$, $u'_5=0$.

$A_5 \cos k(L_2+L_3+L_4+L_5)+B_5 \sin k(L_2+L_3+L_4+L_5) = U_{out}$;

$-A_5 \sin k(L_2+L_3+L_4+L_5)+B_5 \cos k(L_2+L_3+L_4+L_5)=0$

The waveguide-radiator gain factor equals:

$$K = \left|\frac{u_{out}}{u_{in}}\right| = \left|\frac{A_5 \cos k(L_2 + L_3 + L_4 + L_5) + B_5 \sin k(L_2 + L_3 + L_4 + L_5)}{A_1 \cos k L_1 - B_1 \sin k L_1}\right|$$

Here: $F=2/d_n$, $d_n$ is the diameter of the corresponding cylindrical section of the waveguide-radiator, $A_n$ and $B_n$ are the constant coefficients for the corresponding sections of the waveguide-radiator, $L_n$ is the length of the corresponding section of the waveguide-radiator, n is the order number of the waveguide-radiator section, $\alpha$ is the cone index of the waveguide-radiator section with variable cross-section, $u_{in}$ and $u_{out}$ are the amplitudes of displacements at the waveguide-radiator input and output, respectively. The boundary conditions for a force acting on the waveguide-radiator input $F_{in}=0$ and strains $u'_s=0$ at the waveguide-radiator output in this system of equations indicate that the waveguide-radiator has a resonance total length and does not have an acoustic load. From the system of equations (3), one can obtain all necessary characteristics of a five-section waveguide-radiator: lengths and diameters of sections, gain factor, and distribution of vibration amplitudes and strains along the length. From this system of equations, it is also easy to obtain solutions for waveguide-radiators of any type with conical sections (from single-section to five-section waveguide-radiators). Thus, the given system of equations is the most general one. Waveguide-radiators with other shapes of the sections of variable cross-section (for example, with exponential or catenoidal sections) can be considered exactly in the analogous way, taking into account the variation of sound velocity in such sections.

While there has been illustrated and described what are at present considered to be preferred and alternate embodiments of the present invention, it should be understood and appreciated that modifications may be made by those skilled in the art, and that the appended claims encompass all such modifications that fall within the full spirit and scope of the present invention.

What is claimed is:

1. An ultrasonic resonant rod waveguide-radiator having a defined length, an entrance surface and an exit surface, comprising: at least three cylindrical sections, including a first cylindrical section comprising the radiator's entrance surface and a second cylindrical section comprising the radiator's exit surface; at least two sections of variable cross-section;

wherein said at least three cylindrical sections and said at least two sections of variable cross-section are arrayed in alternating positions and acoustically rigidly connected together; wherein the ratio of the cross-sectional areas of the exit surface and the entrance surface is approximately 1:1; wherein the waveguide-radiator's total length is equal to a multiple of half the length of an acoustic wave in the waveguide-radiator material, taking into account a geometrical dispersion; wherein the length of each of said at least two section of variable cross-section is no less than the value of Log(N)/k, where N is the ratio of diameters of the cylindrical sections adjacent to said section of variable cross-section and where k is the wave number, which is equal to $\omega/C$ where $\omega$ is the frequency of ultrasonic vibrations and C is the speed of sound in liquid;

wherein the sum of the length of the second cylindrical section and the length of the section of variable cross-section adjacent to said second cylindrical section is at least 30% of the total length of the waveguide-radiator.

2. The ultrasonic resonant rod waveguide-radiator of claim 1 further comprising resonant plates fastened acoustically rigidly to said second cylindrical section for vibrating at a bending mode.

3. The ultrasonic resonant rod waveguide-radiator of claim 1 further comprising resonant spheres fastened acoustically rigidly to said second cylindrical section for vibrating in a radial mode.

4. The ultrasonic resonant rod waveguide-radiator of claim 1 further comprising a thin plate fastened acoustically rigidly to said second cylindrical section and positioned on said second cylindrical section's side surface in a helix in such a way that the radiating surfaces of the plate are at an acute angle with the axis of the waveguide-radiator.

5. The ultrasonic resonant rod waveguide-radiator of claim 1, wherein said cylindrical sections and said sections of variable cross-section are selected such that the main flux of acoustic radiation into a load additionally is directed through the side surfaces of said waveguide-radiator's second cylindrical section.

6. The ultrasonic resonant rod waveguide-radiator of claim 1 further comprising flexible long waveguides rigidly connected to the exit surface of said waveguide-radiator, said flexible waveguides capable of being excited by said waveguide-radiator's vibration amplitude causing such that said flexible waveguides lose mechanical stability.

7. The ultrasonic resonant rod waveguide-radiator of claim 1 further comprising an ultrasonic reactor having a working medium, said reactor situated within the waveguide radiator and said reactor comprising a hollow resonant sphere acoustically rigidly connected to said waveguide-radiator and being an integral part of said waveguide-radiator.

8. The ultrasonic resonant rod waveguide-radiator of claim 1 further comprising an even number of annular piezoelectric elements situated on said cylindrical sections, for converting electric energy into acoustic energy.

* * * * *